United States Patent [19]

Prior

[11] Patent Number: 5,846,572
[45] Date of Patent: Dec. 8, 1998

[54] BODY FLUID REPLACEMENT SOLUTION

[75] Inventor: Francis George Richard Prior, East Lothian, United Kingdom

[73] Assignee: East & Midlothian NHS Trust, United Kingdom

[21] Appl. No.: 860,366

[22] PCT Filed: Dec. 22, 1995

[86] PCT No.: PCT/GB95/03032

§ 371 Date: Jun. 26, 1996

§ 102(e) Date: Jun. 26, 1996

[87] PCT Pub. No.: WO96/20719

PCT Pub. Date: Jul. 11, 1996

[30] Foreign Application Priority Data

Dec. 30, 1994 [GB] United Kingdom .................. 9426417

[51] Int. Cl.⁶ .......................... A61K 31/70; A61K 33/14; A61K 33/06
[52] U.S. Cl. .......................... 424/620; 424/678; 424/679; 424/681; 514/23
[58] Field of Search .................................. 424/679, 680, 424/678, 681; 514/23

[56] References Cited

U.S. PATENT DOCUMENTS 3,356,570 12/1967 Butcher ...................................... 167/58
4,592,909 6/1986 Winer et al. ............................. 424/127

FOREIGN PATENT DOCUMENTS 2613228 10/1988 France .
2 619 715 3/1989 France .
92/11773 7/1992 WIPO .

OTHER PUBLICATIONS

Abstract—Japanese Patent No. 57091911, Date Jun. 8, 1982, WPI Acc No: 82–58468E.

Abstract—Japanese Patent No. 57091912, Dated Jun. 8, 1982, WPI Acc No: 82–58469E.

Primary Examiner—Phyllis G. Spivack
Attorney, Agent, or Firm—Bell Seltzer Intellectual Property Law Group of Alston & Bird LLP

[57] ABSTRACT

A sterile, pyrogen-free fluid replacement solution for intravenous infusion is disclosed that consists essentially of a physiologically acceptable sodium salt, a physiologically acceptable potassium salt, an osmolality control agent, and, optionally, a component selected from the group consisting of a physiologically acceptable calcium salt and a physiologically acceptable magnesium salt.

9 Claims, No Drawings

BODY FLUID REPLACEMENT SOLUTION

This application is a 371 PCT/GB95/03032 filed Dec. 22, 1995.

The present invention relates to body fluid replacement solutions suitable for intravenous infusion.

The normal metabolism of the human body results in more or less continuous losses of Na (sodium), K (potassium) and water and in order to maintain normal functioning of the body it is essential that the levels of these in the body should be maintained within more or less closely defined limits. Where a patient is unconscious or under a "nil oral intake" regime for one reason or another e.g. pre- or post-operative, then it is necessary for these levels to be maintained by intravenous infusion of suitable solutions. Also in cases of shock it is normal practice to increase the volume of fluid in the circulation in order to maintain blood pressure within safe limits.

Conventional medical practice is based on the administration of standard "quantities of solutions of dextrose (5% w/v aqueous) and physiological saline (0.9% w/v aqueous NaCl), with the occasional addition of potassium salt to one or other of the above solutions. Typically patients are provided daily with 2 liters (4×500 ml units) of dextrose and 1 liter (2×500 ml units) of saline with from 0 to 3 ampoules of aqueous potassium chloride (15% w/v KCl) incorporated into one of the dextrose or saline units. These dosages are however usually applied without regard to the patients' bodyweight which has a substantial effect on the K/Na requirements—e.g. the requirements for a 100 kg patient will generally be 100% higher than those for a 50 kg patient. As a result many patients receive incorrect amounts of K and/or Na. This can have quite serious consequences which can aggravate a patient's condition rather than stabilise or help to improve it. Thus excess Na can result in edema whilst too little Na can give rise to muscular contractions and cramps. High or low levels of K can induce arrhythmias of the heart.

In the past a wide variety of body fluid replacement solutions have been proposed for various purposes. Many of these include bicarbonate ($HCO_3$), stabilized by packing under carbon dioxide ($Co_2$) given in bicarbonate precursors such as acetate or lactate. These can affect the $CO_2:HCO_3$ balance in the body and give rise to adverse effects on the patient if they are not carefully controlled. Such adverse effects can moreover be particularly serious in the case of patients who have an underlying problem such as acidosis resulting from kidney failure or $CO_2$ retention in the lungs, or alkalosis resulting from respiratory problems with excessive loss of $CO_2$ from the lungs. If the solution used has a pH and/or $HCO_3/CO_2$ bias which aggravates that of the underlying condition, then the patient's condition may be seriously exacerbated.

Insofar as bodyfluid replacement solutions are often used in emergency situations and/or in a very routine manner i.e. without detailed consideration of the patient's specific requirements there is accordingly a need for a solution which can be used with a high degree of safety as easily as possible. It is an object of the present invention to avoid or minimize one or more of the abovementioned disadvantages of the prior art.

The present invention provides a sterile pyrogen-free body fluid electrolyte replacement solution for intravenous infusion and consisting essentially of an aqueous solution containing from 30 to 100 mMol Na (per 1000 mls) as a physiologically acceptable salt; from 15 to 50 mMol K (per 1000 mls) as a physiologically acceptable salt; an effective amount of a physiologically acceptable osmolality control agent for providing an osmolality of from 260 to 320 mOsm per kg of solution, said solution being substantially free of material having a molecular weight greater than 5000, and substantially free of any material capable of significantly affecting acid-base balance in vivo.

Thus with a solution of the present invention it is possible to provide effective body fluid replacement and critical electrolyte balance in a safe manner with a minimal risk of undesired complications or adverse effects. Moreover by simply adjusting the volume given approximately to the bodyweight of the patient, optimum body fluid replacement can be achieved in a particularly simple and convenient manner.

Various physiologically acceptable salts may be used in the solutions of the invention though chloride, sulphate and phosphate are particularly convenient, especially chloride.

Whilst it is a particular feature of the present invention that the solutions are substantially free of any other components (thereby minimizing any possible side effects), it will be understood, that other physiologically acceptable substances could be included, if desired, e.g. for nutritional purposes, in small amounts which do not significantly or adversely perturb the metabolism. Thus for example there could be included preferably not more than 5 mMol of calcium and not more than 10 mMol of Magnesium (per litre of solution). Preferably the solutions are substantially free of bicarbonate, and most preferably contain not more than 5 mMol of bicarbonate or a precursor (per liter of solution).

Preferably there is used a non-ionic osmolality control agent, which desirably is substantially water soluble. Suitable agents that may be mentioned include dextrose, fructose, glucose and other sugars which are easily metabolised. Desirably also the agent should be substantially non-vasoactive i.e. does not change the vasculature and the diameter of the veins. Preferably the agent is used in an amount providing an osmolality of from 280 to 300 mOsm per kg of solution.

Whilst the pH of the solutions of the invention will generally be in the range from 5 to 8.5, this is not a particularly critical consideration insofar as the low concentrations of the solution components are more or less readily buffered within the body.

The solution of the present invention is preferably administered at a daily rate of from 20 to 40 mls, preferably 25 to 35 mls, for example about 30 mls, per kg bodyweight of the patient. Thus for a typical bodyweight of 50 kg the preferred daily administration rate would be about 1500 mls, whilst for an 80 kg patient it would be about 2400 mls.

Advantageously the solution of the invention is presented in predetermined volume units of from 1500 to 3500 mls, most preferably about 1500 to 2400 mls, so that a suitable amount for a given patient bodyweight may readily be provided by selecting a suitably sized unit e.g. 1500 mls for around 50 Kg bodyweight (say 45 to 55 Kg bodyweight), 1800 mls for 60 Kg, 2100 mls for 70 Kg, 2400 mls for 80 Kg etc.

In further aspects the present invention provides a method of replacing body fluid and a method of maintaining electrolyte balance, each comprising the steps of determining at least an approximate indication of patient bodyweight, and administering to the patient a solution of the invention at a daily rate of from 25 to 35 mls per kg bodyweight per day.

Ideally the solution of the invention is administered more or less continuously i.e. one daily unit is administered over 24 hours. More conveniently though the solution may be administered over a period of at least 14 hours, preferably from 14 to 28 hours.

Further preferred features of the invention will appear from the following detailed examples given by way of illustration only alongside an example of the prior art.

EXAMPLE 1

Prior Art Design of Fluid Therapy Regimen

Most patients are given three liters of IV fluid daily.

| | |
|---|---|
| 1 × 500 ml normal saline infusion | followed by |
| 1 × 500 mg glucose 5% infusion | followed by |
| 1 × 500 ml glucose 5% infusion | followed by |
| 1 × 500 ml saline infusion | followed by |
| 1 × 500 ml glucose 5% infusion | followed by |
| 1 × 500 ml glucose 5% infusion | |

One or two ampoules of 15% potassium chloride infusion may or may not be added to one or more of these infusions to provide the potassium requirement.

IV fluid therapy in this situation requires six prescription lines to be written, six changes of container for the patient, six entries on the fluid balance charts and up to perhaps two aseptic manipulations in order to add the potassium chloride injection into the regimen. Little attention is paid to providing amounts of water, sodium or potassium which are appropriate for the individual patient. Fluid overload and oedema are not surprisingly common problems in the hospital ward situation.

EXAMPLE 2

Body Fluid Replacement Solution

A body fluid replacement solution was prepared using BP or USP or some other pharmaceutically accepted grade ingredients as follows under sterile conditions and sealed into a conventional body fluid container in the form of a sterile plastics bag provided with adapter means for coupling to a giving set or the like. The solution was prepared using sodium chloride 3.861g, potassium chloride 2.475g and glucose 18.5g in 1 liter of water for injections. A range of predetermined volumes of this standard solution was made available to broadly satisfy the baseline water, sodium, and potassium requirements of various weights of patient as follows:

| Patient weight range | Appropriate volume |
|---|---|
| 45–55 kg | 1500 ml |
| 55–65 kg | 1800 ml |
| 65–75 kg | 2100 ml |
| 75–85 kg | 2400 ml |

The above described solution had a sodium content of 66.7 mMol, potassium content of 33.3 mMol, chloride content of 100 mMol and glucose content of 102.5 mMol per liter, an osmolality of 290 mOsm/kg, and contained less than 0.01% of other components.

EXAMPLE 3

Use of Body Fluid Replacement Solution

A suitably sized body fluid replacement solution unit from Example 2 was selected according to the patient's bodyweight (e.g. a 1500 ml unit for a 48 kg patient) to provide the complete daily requirement for that patient in one single container. The solution may be administered in conventional manner but with the significant advantages that only one bag will be required each day to provide the patients daily baseline requirements so that there is only one prescription line required, one entry on the patient's fluid balance chart and one change over of giving set required each day. The new solution thus simplies IV fluid therapy while providing a more physiologically suitable solution for the patient.

EXAMPLE 4

Clinical Trial Comparison of Use of Body Fluid Replacement Solutions of the Invention and Conventional Intravenous Infusion Therapy A clinical trial on the safety of the new invention solutions was carried out. After obtaining patient consent, a group of approximately 100 surgical patients undergoing laparoscopic cholecystectomy were randomised into: a control group which would receive conventional IV infusion therapy, or a trial group receiving body fluid replacement solutions according to the present invention. 50 patients were allocated into each group.

The conventional therapy was generally 3 liters of fluid per day comprised of 2×500 ml infusions of sodium chloride 0.9% w/v and 4×500 ml of dextrose 5% w/v infusion.

The solution units according to the present invention were selected dependent on patient weight as follows:

| Invention Solution | Patient weight(Kg) | sodium (mMol) | potassium (mMol) | volume (ml) |
|---|---|---|---|---|
| "50 kg" | 45–54 | 100 | 50 | 1500 |
| "60 kg" | 55–65 | 120 | 60 | 1800 |
| "70 kg" | 65+ | 140 | 70 | 2100 |

Each solution was adjusted to an osmolality of 290 with glucose (dextrose). One appropriate solution unit was administered each day over a period of 24 hours at a constant rate. Patients were closely observed for signs of hyper or hypokalaemia, hyper or hyponatremia and any fluid imbalance problems.

Biochemical Monitoring

Daily blood samples were taken from all the patients for the duration of the fluid replacement therapy. These were analysed for plasma sodium, potassium, glucose, creatinine and urea values and the change in concentration in mMol/liter, relative to the patient's initial starting value, was noted.

| Biochemical Monitoring Results | | | | |
|---|---|---|---|---|
| | day 1 | day 2 | day 3 | day 4 |
| 1. Sodium (Normal range: 135 to 145 mMol/liter) | | | | |
| Invention solution | | | | |
| Change in sodium | 0.22 | 0.92 | 0.72 | 0.33 |
| Standard deviation | 1.69 | 2.32 | 2.06 | 1.77 |
| Conventional IV therapy group | | | | |
| Change in sodium | 0.26 | 0.74 | 0.51 | 0.25 |
| Standard deviation | 1.06 | 2.64 | 1.5 | 1.01 |
| 2. Potassium (Normal range: 3.5 to 5.5 mMol/liter) | | | | |
| Invention solution group | | | | |
| Change in potassium | 0.045 | 0.05 | 0.06 | 0.02 |
| Standard deviation | 0.293 | 0.22 | 0.25 | 0.27 |
| Conventional IV therapy group | | | | |
| Change in potassium | 0.005 | 0.05 | 0.05 | 0.005 |

-continued

Biochemical Monitoring Results

|  | day 1 | day 2 | day 3 | day 4 |
|---|---|---|---|---|
| Standard deviation | 0.256 | 0.25 | 0.25 | 0.13 |

3. Urea (Normal range: 3 to 5 mMol/liter)

Invention Solution

| Change in urea | 0.23 | 0.15 | −0.18 | −0.3 |
|---|---|---|---|---|
| Standard deviation | 1.0 | 1.43 | 1.57 | 1.4 |

Conventional IV Therapy Group

| Change in urea | −0.64 | −0.90 | −1.06 | −1.55 |
|---|---|---|---|---|
| Standard deviation | 0.53 | 0.98 | 1.24 | 0.96 |

There were no significant differences between the changes in the sodium and potassium levels between the invention solution group and the conventional therapy group. However, there was a significant difference in the two groups in the urea level. A decrease in urea level is one of the biochemical signs of overhydration. The conventional therapy group indicated a significant number of patients to be overhydrated. In addition the longer the therapy was given the greater the extent to which this problem developed.

Comparison of the time involved in set up and recording of conventional IV therapy and use of inventions solutions.

The amount of time taken to set up the invention solution treatment and the conventional therapy was recorded and the following results obtained.

Setting up time in a 24 hour period

Time to set up

| invention solution bag | 3 mins |
|---|---|
| conventional therapy | 18 mins |

Time to prepare prescription

| invention solution | 2 mins |
|---|---|
| conventional therapy | 8 mins |

Time to record fluid administration

| invention solution | 4 mins |
|---|---|
| conventional therapy | 24 mins |

Total time for implementing body fluid replacement

Invention solution system = 9 mins
Conventional IV therapy = 50 mins

The invention solution system is therefore far less time consuming to set up and record than conventional therapy.

Conclusions

The trial demonstrated no significant changes in plasma urea and electrolytes in those patients receiving the invention solution and confirms that it effectively maintains the required levels. The drop in urea with the conventional therapy group confirms the suspicion that the latter frequently results in fluid overload in a significant number of patients. The invention solution system takes significantly less time to set up and make the relevant recordings than does the conventional therapy.

I claim:

1. A sterile pyrogen-free body fluid replacement solution for intravenous infusion consisting essentially of from 30 to 100 mMol Na (per 1000 mls) as a physiologically acceptable salt; from 15 to 50 mMol K (per 1000 mls) as a physiologically acceptable salt; an effective amount of a physiologically acceptable osmolality control agent for providing an osmolality of from 260 to 320 mOsm per kg of solution, said solution being substantially free of material having a molecular weight greater than 5000, and substantially free of in vivo pH biasing agent and in vivo bicarbonate-carbon dioxide balance biasing agent; and, optionally, a component selected from the group consisting of not more than 5 mMol of calcium and not more than 10 mMol of magnesium (per 1000 mls) as a physiologically acceptable salt.

2. A solution as claimed in claim 1 wherein each said physiologically acceptable salt is selected from chloride, sulphate and phosphate.

3. A solution as claimed in claim 1 wherein said osmolality control agent comprises a non-ionic osmolality control agent.

4. A solution as claimed in claim 3 wherein said agent is substantially water soluble.

5. A solution as claimed in claim 4 wherein said agent comprises an easily metabolized sugar.

6. A solution as claimed in claim 5 wherein said agent is substantially non-vasoactive.

7. A solution as claimed in claim 3 wherein the agent is used in an amount providing an osmolality of from 280 to 300 mOsm per kg of solution.

8. A solution as claimed in claim 3 which solution contains not more than 5 mMol of bicarbonate or a precursor thereof (per 1000 mls of solution).

9. A solution as claimed in claim 1 which is substantially free of each of bicarbonate, lactate and acetate.

* * * * *

UNITED STATES PATENT AND TRADEMARK OFFICE
CERTIFICATE OF CORRECTION

PATENT NO. : 5,846,572
DATED : December 8, 1998
INVENTOR(S) : Prior

It is certified that error appears in the above-identified patent and that said Letters Patent is hereby corrected as shown below:

<u>Title page, Item [86],</u>
Lines 2 and 3,
"June 26, 1996", each occurance, should read -- June 26, 1997 --.

Signed and Sealed this

Sixteenth Day of October, 2001

Attest:

*Attesting Officer*

NICHOLAS P. GODICI
*Acting Director of the United States Patent and Trademark Office*